United States Patent [19]

Miller et al.

[11] 4,302,222
[45] Nov. 24, 1981

[54] METHODS AND APPARATUS FOR CONTINUOUS PREPARATIVE CHROMATOGRAPHIC SEPARATION OF FLUID MIXTURES

[75] Inventors: Bernard Miller; Henry L. Friedman, both of Princeton, N.J.; Charles H. Meiser, Jr., Yardley, Pa.

[73] Assignee: Textile Research Institute, Princeton, N.J.

[21] Appl. No.: 121,775

[22] Filed: Feb. 14, 1980

[51] Int. Cl.³ .............................................. B01D 15/08
[52] U.S. Cl. ........................................ 55/67; 55/386; 55/390
[58] Field of Search ........................... 55/67, 386, 390

[56] References Cited

U.S. PATENT DOCUMENTS

| | | | |
|---|---|---|---|
| 1,985,204 | 12/1934 | Derr et al. | 369/917 X |
| 2,743,818 | 5/1956 | Higuchi | 55/67 X |
| 2,882,244 | 4/1959 | Milton | 252/455 |
| 2,893,955 | 7/1959 | Coggeshall | 55/67 X |
| 2,913,501 | 11/1959 | Cahill | 568/919 X |
| 2,965,680 | 12/1966 | Anderson et al. | 568/919 X |
| 3,366,582 | 1/1968 | Adams et al. | 55/35 X |
| 3,408,267 | 10/1968 | Miller et al. | 203/19 |
| 3,766,660 | 10/1975 | Settlemyer | 55/74 X |

Primary Examiner—John Adee
Attorney, Agent, or Firm—John J. Kane; Frederick A. Zoda; Albert Sperry

[57] ABSTRACT

Two processes and apparatus for chromatographically separating components of a volatilizable mixture on a continuous basis are described herein as specific examples of the continuous preparative chromotographic separation of unwanted volatile species from volatile product by passage through a continuous fibrous textile solid. The volatilized mixture is fed by means of a flowing carrier gas through a column or conduit containing continuous polymeric solid therein such as a fibrous textile solid like yarn wherein one unwanted component of the mixture is significantly retarded in its passage by adsorption processes as compared to the other components of the mixture. The retarded component is that which one wishes to remove from the mixture. The desired product is gathered at the outlet of the conduit. The polymeric solid separating medium is regenerated by removal of the adsorbed component in either of two ways. In one method the adsorbing material is arranged in a continuously moving closed loop so that the adsorbed species can be stripped from it at a different location without interfering with continuous separation. The regenerated adsorbent is then returned to the point where it can serve to separate more of the mixture. In an alternate procedure, the adsorbed species is removed from a stationary adsorbing material by backflushing with carrier gas once the desired product has cleared. The column is then ready to receive a new charge of feed mixture. The conduit is preferably heated to control the movement of the various species so as to optimize the efficiency of separation. The major case to which these methods have been applied is the removal of water from a mixture with ethanol.

37 Claims, 2 Drawing Figures

U.S. Patent  Nov. 24, 1981  4,302,222
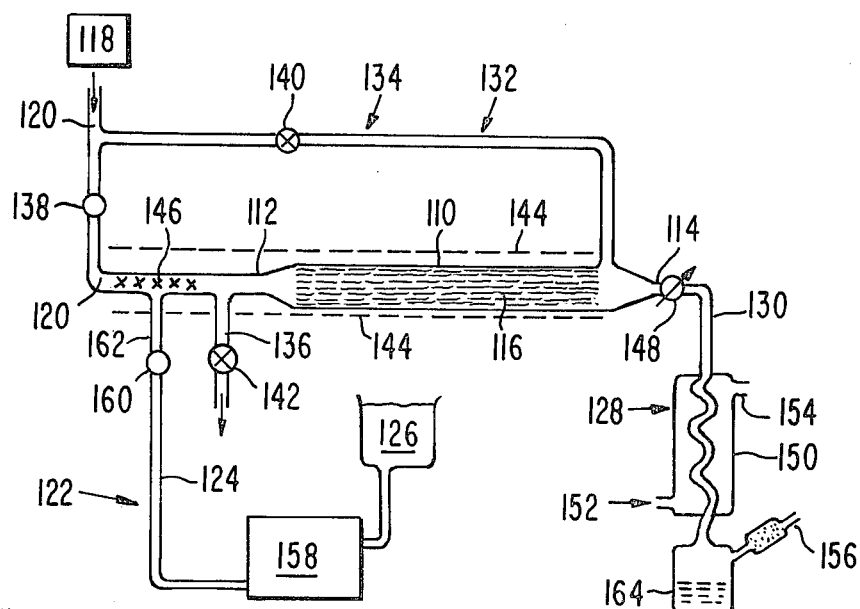
*Fig_1*
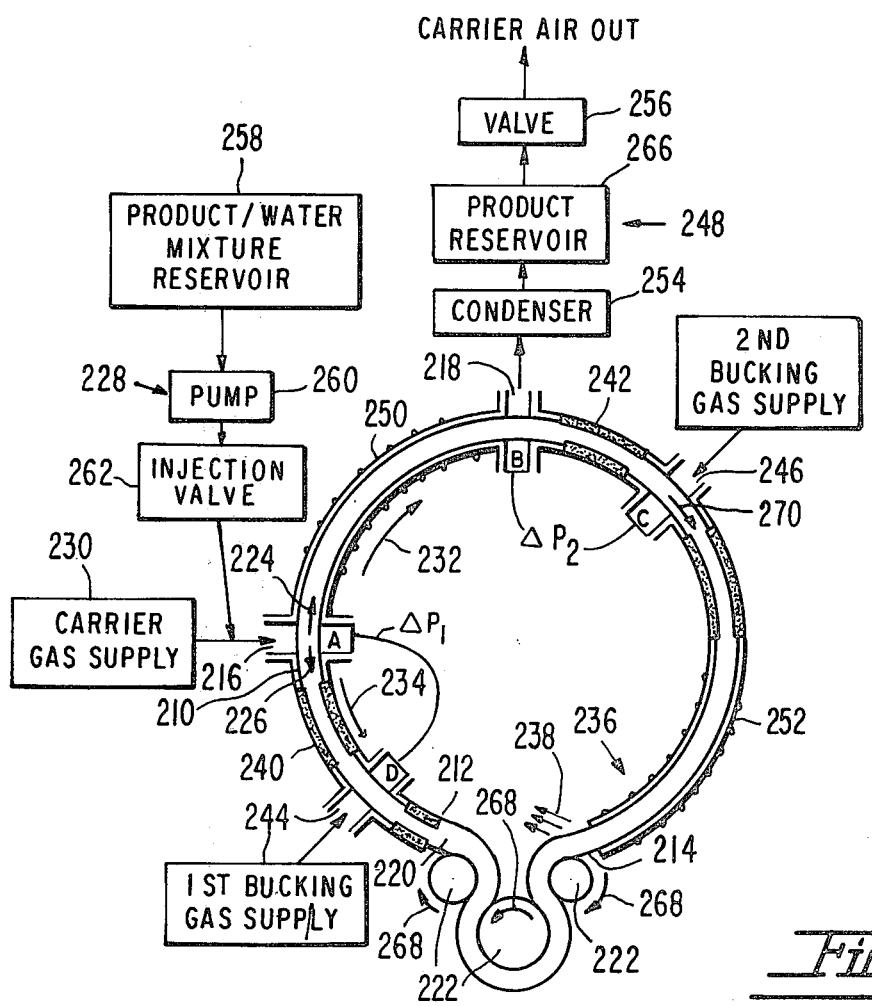
*Fig_2*

METHODS AND APPARATUS FOR CONTINUOUS PREPARATIVE CHROMATOGRAPHIC SEPARATION OF FLUID MIXTURES

BACKGROUND OF THE INVENTION

1. Field of the Invention

The present invention deals with the general field of separation of components utilizing chromatographic columns wherein various solid materials are placed within the columns to detain components of a moving mixture to different degrees so that they will become separated during passage through the column. Basically, such separation always is possible within a column containing the given solid absorbent whenever one component has a rate of passage that is significantly different from that of another component. In theory, any two such components can be separated given a long enough column. The present invention provides a novel convenient way to form and use such packed columns of any desirable length within practical space limitations, and also provides two novel processes and approaches whereby continuous separation of volatile mixtures can be performed.

2. Description of the Prior Art

Devices in the prior art have been patented such as U.S. Pat. No. 1,985,104; 2,882,244; 2,913,501; 2,965,680, 3,366,582; 3,408,267; and 3,766,660.

The formation of chromatographic columns having a solid absorbent enclosed in a conduit is old in the art. Normally, when such processes have utilized solid polymeric packing material it has been in the form of granules or pellets. When fibrous packing was used, the fibers have been packed isotropically as individual elements in the same manner as other granular material. For example, when textile yarns were the source of the packing material, they were first chopped into small discrete pieces. Whatever the nature of the individual packing elements, it has always been necessary to take pains that the packing was uniform across and through the column, which necessitated slow and careful filling procedures and limited the practical length of column which could be used without excessive resistance to flow. The present invention provides a means for much more easily packing such columns by using continuous yarns which permits the use of columns of much greater length than hitherto possible.

Heretofore the main problem with the use of such systems for continuous separation of mixtures has been the removal of the adsorbed component from the column quickly enough so that it will not interfere with the separation of the next mixture charge. If this cannot be done the column packing will soon become saturated and will not perform its separating function. The present invention teaches that certain types of continuous polymeric materials and continuous fibrous textile solids that do not irreversibly adsorb volatiles can be made to retard the passage of certain species to a greater or lesser degree depending on certain controllable variables, e.g., temperature. This effect plus the use of two novel mechanical arrangements have been used to quickly regenerate such columns so that they will be available to receive and process an unlimited series of charges of feed mixture.

SUMMARY OF THE INVENTION

The present invention generally provides a novel method of using fibrous textile solids, such as textile yarns for chromatographic separation of multicomponent chemical mixtures. There are many different types of textile yarns and other fibrous solids usable in this method. In order to be usable it is only necessary that the passage times through the given continuous fibrous solid be different for the two or more components being separated. The following tables disclose passage times of certain chemical components through various types of continuous fibrous textile solids. Although many of the examples of methods and apparatus shown and disclosed in the present invention illustrate the separation of ethanol from water using rayon yarns, the examples given below show that separation can be achieved for many different vapors and using yarns made from various polymers.

| PEAK PASSAGE TIMES THROUGH RAYON YARN COLUMNS* | | |
|---|---|---|
| | Column Length | |
| Probe | 12 ft | 1 ft |
| Air | 0.32 min | 1-2 s |
| Chloroform | 0.35 min | |
| Formaldehyde | 0.35 min | |
| Methanol | 0.35 min | |
| Ethanol | 0.40 min | 0.15 min |
| Hexane | 0.50 min | |
| Ammonia | 1.35 min | |
| Water | 45.0 min | 4.0 min |

*Rayon yarn packed in 2.1 mm I.D. tubing. One microliter of probe injected into carrier gas flowing at 0.7 ml/s. Column at 110° C.

| PEAK PASSAGE TIMES THROUGH OTHER YARN COLUMNS* | |
|---|---|
| Polyester Yarn | |
| Probe | Peak Time |
| Air | 0.08 min |
| Water | 0.18 min |
| Ethanol | 0.04 min |
| Hexane | 0.06 min |
| Tetrachloroethane | 0.12 min |
| Nylon Yarn | |
| Probe | Peak Time |
| Air | 0.06 min |
| Water | 0.49 min |
| Ethanol | 0.06 min |
| Hexane | 0.04 min |
| Tetrachloroethane | 0.10 min |
| Polyacrylic Yarn | |
| Probe | Peak Time |
| Air | 0.06 min |
| Water | 0.32 min |
| Ethanol | 0.05 min |
| Hexane | 0.05 min |
| Tetrachloroethane | 0.19 min |
| Polypropylene Yarn | |
| Probe | Peak Time |
| Air | 0.05 min |
| Water | 0.08 min |
| Ethanol | 0.08 min |
| Hexane 0.06 min | |
| Tetrachloroethane | 0.65 min |

*Approximately 0.5 g of yarn packed in one-foot long 2.1 mm. I.D. column. 0.1 microliter of probe (1.0 microliter air) injected into carrier gas (Helium) flowing at 0.7 ml/s. Column at 110° C.

The present invention more particularly includes two new methods and apparatus for continuous chromatographic separation of one component of a volatile mixture by virtue of its greater attraction to a continuous polymeric solid positioned throughout the interior of a conduit or column. Fibrous textile solids as the yarns listed above, are particularly suitable as the solid adsorbent. More particularly rayon can be utilized in this manner to remove water from mixtures because such yarns exhibit a highly selective attraction for water vapor while allowing other species even those quite similar to water in size, chemical structure, and boiling point to pass essentially unretarded therethrough. Also accurate control of the adsorbing characteristics of such yarn filled columns can be achieved by controlling the volume of the feed mixture charge, the frequency of charge injection, the pressure within the column, the temperature of the conduit, and the yarn packing density.

The present invention includes two novel devices which provide means for continuous regeneration of the adsorbing medium so that the undesirable component of the feed mixture does not accumulate within the column. This makes these processes suitable for continuous refining operations wherein it is necessary to produce at a downstream end a product free from an undesirable species. The manufacture of ethanol via fermentation processes is an important example where an undesirable component (water) must be removed in order for the product ethanol to be suitable for certain end use as for example a component of motor fuel (e.g., gasohol).

The present invention discloses as one of the processes for separation an apparatus which has a closed loop of continuously moving polymeric solid as the adsorbing medium. Textile materials such as yarns are particularly usable for this purpose because of their flexibility and appreciable tensile strength. This system contemplates the driving of a loop made up of yarns by a drive system such that the loop passes through a conduit which may be of a generally circular path. The basic concept is to cause the unwanted adsorbed species to be transported to a location along the yarn path where it can be removed before that portion of the yarn returns to the point where the product and carrier gas are still within the conduit. With water this amounts to drying of the yarn by exposing it to sufficient heat and air flow during this regenerative part of its cyclic path. Preferably the yarn travels within tubing over most of the path except in that area where it emerges from the tubing or conduit to be engaged by the drive means.

The mixture charge is fed into the carrier gas stream and vaporized before being applied to the yarn loop at one location on its circuit. Vaporization is achieved by maintaining a preheated zone where the feed charges enter the carrier gas flow at a sufficiently high temperature to volatilize all of the entering mixture. This volatilization chamber also contains a metal honeycomb to aid the vaporization process. An injection valve controls the duration of the injection period and, in conjunction with a pump, the amount of feed mixture per charge. The tubing between this valve and the vaporization chamber is a small bore capillary so that very little liquid will remain at this location between injections.

The carrier gas carries the vaporized mixture to the yarn loop inlet and then follows the conduit part way along the loop to an outlet adapted to gather the product. The movement of the carrier and any entrained species is achieved by a pressure differential between the gas source and the product collection chamber. The key feature of this system is that this gas flow moves in a direction counter to that of the yarn during that portion of their paths when they are in contact. In consequence, chromatographic separation occurs on a substrate which is moving countercurrent to the carrier flow. The velocity of the yarn is set so that it will be slower than the chromatographic velocity of the desired product but higher than the chromatographic velocity of the component to be removed. Therefore, the product will move to its exit point on the yarn loop path at a net velocity equal to the difference between the rate it would move through the same substrate if the latter were stationary and the yarn speed. On the other hand, the more highly adsorbed species will have a net velocity vector in the same direction as the yarn moves and in effect will be carried along by the moving yarn. Therefore, what will effectively happen will be a separation of the desired product from the other component at the inlet to the yarn path conduit. The latter is then transported by the yarn to another part of the path where it can be removed which in effect regenerates the yarn so that it can again serve as a separating agent. The product after leaving the loop is collected by a suitable arrangement such as a condensing system or selective adsorbent while the carrier gas is vented preferably to the atmosphere.

To achieve a high yield of product and good control of the process it is necessary to insure that the carrier gas flow and its entrained product move from the inlet to the outlet and then to the collection chamber without any significant losses at the inlet and outlet junction points. This may be accomplished by a combination of two flow directing arrangements: (1) The yarn conduit immediately after the yarn passes the inlet point is constricted so that the yarn passing through it forms a "plug" which will inhibit the flow of gas in that direction. The same type of constriction is used just before the yarn reaches the outlet point to discourage gas from flowing through the rest of the conduit. (2) The system is supplied with two bucking gas supplies. One enters the yarn conduit at a position so that it will oppose any flow of gas from the inlet point in the direction of yarn movement and the other at a point where it will oppose any flow of gas along the yarn path beyond the outlet junction. The adjustment of these two bucking flows may be accomplished by differential pressure guages which indicate whether or not there is any net loss of carrier gas at the two junction points.

The present invention further discloses an alternate means for achieving continuous separation which makes use of a reciprocal flow pattern for the carrier gas through a stationary chromatographic adsorption medium such as a textile yarn bundle. With this system the adsorbent contained within a conduit is totally between the inlet and outlet of the gas flow system. A feed mixture supply line including a suitable pump and valve system injects a charge into the gas line where it is vaporized in the same manner as previously described for the moving yarn system. The carrier gas then carries the vaporized mixture through the inlet of the packed conduit. The more adsorbable species is retarded by the polymeric solid while the other components of the mixture move through without appreciable retardation. For example, under proper conditions, ethanol may be made to pass through a packed column in about 10 seconds while water injected at the same time will not begin to appear at the outlet of the column before about 20 minutes. A product collecting means is connected in fluid flow communication to the outlet of the conduit. The product gathering means preferably includes a condensing or adsorbing collection chamber and a carrier gas vent.

Once the desired product has passed out of the adsorbing column the automatic reciprocating flow system will activate the reverse flow means. This reverse flow means effectively applies the carrier gas flow to what was previously the outlet of the packed conduit so as to backflush the adsorbed species out through the original inlet. A bypass vent immediately adjacent to this inlet is opened during this interval and the undesired component is vented from the system. The flow control means will include a valve within the carrier gas input line which is normally open to allow carrier gas to enter through the inlet but is responsive to close upon activation of the reverse flow means. The reverse flow means further includes a second valve means within the reverse flow feed line which is normally closed and is adapted to open responsive to activation of the reverse flow means to thereby apply the carrier gas to the packed conduit in the reverse direction. The reverse flow means further includes a bypass third valve means which is normally closed and is adapted to open responsive to activation of the reverse flow means. Preferably this outlet is vented to the environment at atmospheric pressure to hasten the expelling of the backflushed component.

Therefore this process basically comprises the applying of a charge of mixture to the inlet of the packed column with the resulting separation by preferential adsorption of one component followed by the gathering of the desired product and the back-flushing of the undesired species from the separating medium. In this fashion a cycle has been completed and the polymeric solid is ready to receive a new charge of mixture.

Both of the above methods for continuous separation are particularly attractive and novel when utilizing a polymer yarn such as rayon which has very high and specific adsorbing power for water. The water will therefore move very slowly along the yarn. For continuous moving yarn system this means that the yarn velocity need not be very high to nullify the chromatographic movement of the water and keep it from following the desired components of the mixture. In the reciprocal flow system the extremely slow movement of water means that it will have penetrated only a short distance through the yarn conduit by the time the desired product has been completely expelled through the outlet. Therefore when the reverse flow means is activated the water will only have a short distance of packing to pass over in order to be expelled through the original inlet of the column. In addition the water during its retreat is passing over surfaces which are already wet and as such the adsorption sites are less in number and the water will be able to pass with less retardation. These systems are extremely advantageous compared with prior art which normally requires waiting until the undesired product was expelled through the original outlet or removed in some other manner which required a considerable amount of time. The present invention provides means for processing and separating an unlimited series of sequential charges with only very short time intervals between charge injections.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a schematic representation of an embodiment of the present invention including a continuous reciprocating flow apparatus for chromatographically separating a more adsorbable species such as water from a less adsorbable volatile product; and FIG. 2 is a schematic representation of an embodiment of the present invention including a continuous flow apparatus for chromatographically separating an unwanted adsorbable species such as water from a volatile product.

DETAILED DESCRIPTION OF THE PREFERRED EMBODIMENT

An embodiment of the reciprocating flow apparatus of the present invention is shown in FIG. 1 wherein a column or conduit means 110 is filled throughout the interior thereof with a continuous polymeric solid or a continuous fibrous textile solid 116. The conduit means defines an inlet 112 for receiving volatilized mixtures of a volatile species such as water and a volatile product. The conduit means 110 also defines an outlet 114 for gathering the product therefrom.

A carrier gas supply means 118 provides carrier gas through a carrier gas input line 120. A mixture supply means 122 supplies mixture from a mixture reservoir 126 through a mixture supply line 124. Preferably the mixture is fed by way of a pump means 158 which moves the mixture through the mixture supply line 124 to an injection valve means 160. This mixture then passes through the capillary restriction means 162 to enter into the carrier gas input line 120. To facilitate vaporization a heating means 114 may be positioned at the junction between the capillary restriction means 162 and the carrier gas input line 120 to increase the temperature of the mixture as it passes into the carrier gas. To further aid in vaporization the carrier gas input line 120 can include a wool packing means 146 such as a steel wool material or the like to provide additional heated surface area to aid in vaporization of the mixture. The carrier gas then conveys the vaporized mixture into the inlet 112 of the conduit means 110.

The continuous polymeric solid 116 within the conduit is preferably a yarn material and more particularly is preferably of rayon when specifically used to separate a volatile species from water such as ethanol. The adsorbing characteristic of rayon particularly with respect to water will make the migration time of water through the length of the conduit substantially greater than the migration time of the product therethrough. Therefore as the carrier gas passes through the polymeric solid 116 the water will be retained in the leading edge thereof. The product will then pass outward through outlet 114 and be gathered by product gathering means 128. The product gathering means includes an outlet line 130 in fluid flow communication with a cooling means 150 which may be used to condense the vaporized product. The cooling means will include a coolant inlet 152 and a coolant outlet 154. The product will be gathered within a product reservoir 164 and a carrier gas vent 156 will be included near the product reservoir 164 to remove the carrier gas from the product. The product gathering means may further include a flow control valve means 148 which is variably positionable to control the speed of carrier gas flow in the forward direction through the continuous polymeric solid 116 within conduit means 110.

The above description has illustrated the forward flow portion of the cycle of operation of the reciprocating flow apparatus and process. Once the product has completely passed through the outlet 114, the reverse flow means 132 will be activated to initiate the second or reverse flow portion of the cycle. When the reverse flow means 132 is actuated the normally open first valve means 138 within carrier gas input line 120 will be closed. On the other hand, when reversing flow means 132 is activated the second valve means 140 within reverse flow line 134 and the third valve means 142 within bypass vent 136, which are both normally closed, will be caused to open. With the closing of valve 138 and the opening of valves 140 and 142 a reverse flow path will be established through the conduit means 110 to backflush the water adsorbed to the rayon or other polymer adsorbent therein. In the reversing flow setup the carrier gas will pass from carrier gas supply means 118 through reverse flow line 134 into the conduit 110 near the outlet 114 thereof. This carrier gas will then flow through the continuous polymeric solid 116 in a reverse direction and out through the inlet 112 carrying the water which has been adsorbed to the polymer solid outward therewith. The water will then be caused to be carried through bypass vent 136 and through the now open valve 142 to be exhausted and expelled or collected as desired. The back flow of carrier gas and water up the carrier line 120 will be prevented by valve 138 being closed. Similarly the back flow of carrier gas and water into mixture supply line 124 will be prevented by the closed valve 160 within the mixture supply line 124 adjacent the carrier gas line 120.

At this point the complete cycle will be completed. This process is much quicker than possible by waiting until the water passes through the outlet of the conduit 110 since the adsorption of rayon for water is quite strong. Therefore it is desirable to backflush and cause the water to pass over the already wetted continuous polymeric solid 116 which has a limited number of unfilled adsorption sites. Therefore by backflushing or reverse flow the time required to ready the conduit 110 and the polymeric solid 116 to receive a new charge of mixture from reservoir 126 is substantially decreased.

FIG. 2 illustrates an embodiment of a continuous flow apparatus for chromatographically separating water from volatile products which includes a conduit 210 which may be configured in an approximately circular configuration having a first open end 212 and a second open end 214. The conduit contains a closed loop 220 of continuous polymeric solid such as a rayon yarn or the like. This closed loop is adapted to be driven by a driven means 222 which may be a friction drive or the like. The drive means is most easily secured for friction drive to the closed loop 220 at a location outside of the conduit 210 between first open end 212 and second open end 214. A carrier gas supply means 230 is positioned to supply carrier gas to the inlet 216 of the conduit 210. A mixture supply means 228 may include a mixture reservoir 258, a pump means 260 to remove the mixture from the reservoir 258 and an injection valve 262. The mixture within reservoir 258 is of water and a volatile product such as alcohol or the like. This mixture is pumped by pump means 260 from the reservoir through valve 262 into the carrier gas line which is heated and packed with metal honeycomb or wool so as to vaporize the charge before it reaches the conduit 210 at the inlet location 216. The pressure at which the carrier gas is supplied to inlet 216 is sufficiently greater than the pressure at outlet 218 such that a flow from the inlet to the outlet of the carrier gas and the mixture is encouraged.

The drive means 222 is driven in the drive direction shown by arrows 268 such that the closed loop 220 of continuous polymeric solid moves in the downstream direction 234 from the outlet 218 to the inlet 216. By this definition the upstream direction 232 will be in the clockwise direction as shown in FIG. 2. The velocity of movement of the closed loop 220 is of a significant value since it must be less than the migration velocity of the product through the continuous polymeric solid. Also this loop velocity must be greater than the migration velocity through the polymeric solid of the unwanted species, in this embodiment, water. By choosing the velocity in this fashion the resultant velocity of the product will be in a direction shown by arrow 24 upstream from inlet 216. On the other hand the resultant velocity direction 226 of the water within the volatilized mixture will be in the direction downstream from the inlet 216. In this manner there will be an immediate separation of the water from the product upon passage through inlet 216 into the conduit 210. The velocity in direction 224 of the product will be equal to the difference between the migration velocity of the product through the loop 220 and the movement velocity of the loop. At this velocity the product will be carried from inlet 216 to outlet 218 to be gathered by the product collecting means 248. Product collecting means 248 may include a condenser 254 for condensing the volatilized product and a product reservoir 266 for collecting the product as well as a valve means 256 for removing carrier gas from the collected product within reservoir 266. The speed of migration of the product from the inlet 216 to the outlet 218 may be controlled by a first heating means 250 positioned adjacent the moving loop 220.

The water of the mixture will be carried by loop 220 to a water expelling means 236. This expelling means preferably includes a second heating means 252 for further volatilizing the water within the loop and expelling it in the direction shown by arrows 238.

A first constriction means 240 may be positioned immediately downstream of inlet 216 in order to urge the carrier gas to flow toward the outlet and not in the other direction from the inlet. This constriction means 240 effectively forms a plug of continuous polymeric solid 220 as it passes therethrough to urge the carrier gas and product to flow from inlet 216 to outlet 218. To further urge this inlet to outlet flow a first bucking gas supply 244 may be admitted into the conduit 210 at a position immediately downstream of the inlet to assure that pressure sensed at point D is at least as great as the pressure sensed at point A so that $\Delta P_1$ is approximately zero. In this manner the carrier gas and product will be further urged to flow directly from the inlet to the outlet.

In a similar fashion it is desirable to prevent any carrier gas or product from flowing from the inlet past the outlet through conduit 210. To minimize this flow a second constriction means 242 may be positioned immediately upstream of outlet 218. Also a second bucking gas supply means 246 may be positioned immediately upstream of the outlet to encourage carrier gas and product to flow through the outlet and be gathered within the product reservoir 266. This second bucking gas supply also provides a second function in that it may provide a gas flow of some value downward in the direction shown by arrow 270 to force volatilized water which has been heated by second heating means 252 to be expelled outwardly into the environment in the direction shown by arrows 238. Also second bucking gas supply 246 should be kept to a sufficient flow to keep $\Delta P_2$ or the differential pressure between points B and C approximately zero to encourage flow of carrier gas and product through outlet 218.

An analysis of the use of the closed loop design is shown on the below table.

| | ENRICHMENT AND YIELD OF A 50% AQUEOUS ETHANOL MIXTURE | | | | |
|---|---|---|---|---|---|
| Run No. | Separation Column temp,°C. | Yarn Vel., mm/s | Drying air flow, ml/s | Product % ethanol | % yield |
| 1 | 110 | 8 | 5 | 78 | 73 |
| 2 | 98 | 8 | 5 | 90 | 52 |
| 3a | 110 | 8 | 11.7 | 84 | 80 |
| 3b | 110 | 8 | 11.7 | 82 | 77 |
| 4 | 110 | 8 | 18.3 | 86 | 78 |
| 5 | 98 | 8 | 18.3 | 92 | 85 |
| 6 | 86 | 8 | 18.3 | 96 | 80 |
| 7 | 86 | 5 | 18.3 | 95 | 87 |

The above eight runs are shown with varying column temperatures and yarn velocities as well as variable speeds of flow of the drying air. The input mixture was a 50% aqueous ethanol mixture and the product results are shown in the rightmost column of this table. In particular the percentage ethanol indicates exactly that percentage of ethanol which was in the resultant product and the percentage yield shows that amount of ethanol of the original mixture which was yielded in the resultant product. There are other variables which can be altered to increase the percentage ethanol and yield of the resulting product, however, this table shows only the responses for three of those variables. In particular, this table shows in runs 1 and 2 that the lowering of the separation column temperature effectively increases the percentage of alcohol in the product but lowers the yield thereof. This occurred during these runs because the chromatographic velocities of both components were reduced but more so for the water. Runs 3a and 3b show the reproducability of these experiments. Runs 1, 3 and 4 show that increasing the drying air flow rate has the effect of enriching the product in alcohol. This is interpreted to mean that the yarn was not completely dried at low drying air flows and that the residual water was carried over and partially taken up by the carrier stream. Comparing runs 4, 5 and 6 reveals that at the most rigorous yarn drying condition the enrichment effect of lowering the separation coluum temperature is quite noticeable. Namely, 86° C. results in a product containing 96% alcohol. Finally, it can be determined that a reduction in yarn speed effectively increases the yield without lowering the concentration of alcohol in the product. These results can be taken as a strong indication that in this example of the complete separation of alcohol from water, recovery of at least 90% of the alcohol can be achieved regularly by the proper combination of controllable process parameters.

The continuously moving closed loop of continuous polymeric solid can be particularly usable for dehumidification. In particular, the use of rayon would be preferable but not required due to its high adsorption characterisics with respect to water. In particular, by exposing the moving loop to humid air the water tend to be withdrawn therefrom to adhere to the adsorption sites of the rayon. The movin loop will then carry this adsorbed water to another point along the path of movement of the loop at which this water will be withdrawn. In this manner the high adsorption characteristics of rayon or another continuous polymeric solid with respect to water will be utilized by movement through a closed loop to provide an efficient process for dehumidification.

It should be appreciated that the apparatus and processes of the present invention are particularly usable with rayon yarn but is also usable with other yarns such as nylon as well as many other continuous polymeric solids. The invention is also primarily usable for the separation of any preferentially adsorbable volatile species such as water from ethanol or alcohol but may be used to separate any volatile product from any volatile species. It should also be appreciated that the phase of the mixture during separation in the illustrated embodiments is gaseous. However, similar separations of components in the liquid phase by comparable exposure to yarn or other selective adsorbents are conceivable especially when a countercurrent moving adsorbent is used.

One of the primary novel characteristics of the present invention is the usage of a polymeric solid which is continuous such as textile yarns. Such continuous solids are more easily packed within the conduit and have been proven to expose sufficient adsorption sites to substantially reduce the flow rate of water in comparison with the chromatographic flow rate of other volatile species even those species having similar chemical characteristics to water.

Furthermore, the actual cross-sectional shape of the conduit of the circular system or the conduit of the reciprocating system has been circular. However, this cross-section could be of any desired geometric configuration especially when such conduits are utilized in large multiple banks.

The constriction means are preferably of a plastic material such as polytetraflouroethylene to minimize the friction of pulling the yarn therethrough. However, these means can be chosen of any material necessary in order to form the constriction plug of the solid material of the closed loop when passing therethrough.

The carrier gas utilized usually has been air since it is readily available and relatively inexpensive. Of course any gas supply can be used. This also applies to the two bucking gas supplies utilized in the continuous system which are preferably air but can be chosen as any gas. Further in the continuous system, the chosen configuration has been circular however, the path of the closed loop can be of any desired shape including the basic elements as claimed.

The present invention provides the first usage of continuous polymeric solids such as intact yarns to pack columns for chromatography. Prior art usages have been limited to chopped-up or ground-up polymers. Also the present invention makes use of the appreciable flexibility and tensile strength of yarns to aid in the packing of the conduits and in the movement of the yarn through the closed loop path in the continuous system.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

We claim:

1. A continuous reciprocating flow apparatus for preparative chromatographic separation of an unwanted volatile species from a volatile product comprising:
   (a) a conduit means defining an inlet and an outlet therein;
   (b) a continuous polymeric solid positioned throughout the interior of said conduit means;
   (c) a carrier gas supply means including an input line extending in fluid flow communication to said input of said conduit means to supply carrier gas thereto;
   (d) a mixture supply means including a mixture supply line means in fluid flow communication with said input line of said carrier gas supply means and with a reservoir containing the mixture of volatile species and volatile product, said mixture supply means adapted to supply volatilized mixture to said input line for communication therethrough to said inlet of said conduit means;
   (e) a product gathering means including an outlet line in fluid flow communication with said outlet of said conduit means;
   (f) a reverse flow means adapted to selectively reverse the flow of carrier gas through said continuous polymeric solid within said conduit means to withdraw the volatile species accumulated therein, said reverse flow means comprising:
   1. a reverse flow line extending from said carrier gas input line to said outlet of said conduit means;
   2. a bypass vent in fluid flow communication with said carrier gas input line adjacent said inlet of said conduit means, said bypass vent adapted to gather volatile species expelled through said inlet during reverse flow through said conduit means;
   3. a first valve means positioned within said carrier gas input line upstream of said bypass vent, said first valve means being normally opened and adapted to close responsive to actuation of said reverse flow means;
   4. a second valve means positioned within said reverse flow line, said second valve means being normally closed and adapted to open responsive to actuation of said reverse flow means; and
   5. a third valve means positioned within said bypass vent, said third valve means being normally closed and adapted to open responsive to actuation of said reverse flow means.

2. The apparatus as defined in claim 1 further comprising a heating means positioned adjacent said conduit means to control the temperature thereof and positioned adjacent said carrier gas input line at the location of fluid flow connection to said mixture supply line to facilitate the volatilizing of the mixture into the carrier gas.

3. The apparatus as defined in claim 2 further comprising metal wool packing located within said carrier gas input adjacent connection to said mixture supply line to facilitate volatilizing of the mixture into the carrier gas.

4. The apparatus as defined in claim 1 wherein said continuous polymeric solid comprises yarns of any fiber-forming polymer.

5. The apparatus as defined in claim 1 wherein said continuous polymeric solid comprises yarns of rayon.

6. The apparatus as defined in claim 1 wherein said product gathering means includes a flow control valve means adjacent said outlet of said conduit means to control flow therethrough.

7. The apparatus as defined in claim 1 wherein said product gathering means includes a cooling means to condense volatilized product.

8. The apparatus as defined in claim 7 wherein said product gathering means includes a carrier gas vent to release the carrier gas after the product has been collected.

9. The apparatus as defined in claim 1 wherein said mixture supply means includes a pump means to convey the mixture through said mixture supply line.

10. The apparatus as defined in claim 1 wherein the volatile species is water.

11. The apparatus as defined in claim 10 wherein said mixture supply means includes a capillary restriction means positioned between said injection valve means and said carrier input line to minimize back flow therethrough and to minimize volatilizing of the mixture except when a charge of mixture is being fed therethrough by said injection valve means.

12. The apparatus as defined in claim 1 wherein said mixture supply means includes a mixture reservoir in fluid flow communication with said pump means.

13. The apparatus as defined in claim 1 wherein said bypass vent is vented to the atmospheric environment.

14. The apparatus as defined in claim 10 wherein said injection valve means intermittently supplies charges of mixture to said carrier gas input line.

15. The apparatus as defined in claim 14 wherein said reverse flow means is responsive to actuate after a predetermined time delay subsequent to the supplying of a charge of mixture wherein the delay is long enough to allow the product within the mixture charge to be gathered by said product gathering means and short enough to have the volatile species still retained within the adsorbing continuous polymeric solid.

16. The apparatus as defined in claim 1 wherein the carrier gas is air.

17. A continuous reciprocating flow apparatus for preparative chromatographic separation of unwanted water from a volatile product comprising:
   (a) a conduit means defining an inlet and an outlet therein;
   (b) a continuous polymeric solid comprising yarns of rayon positioned throughout the interior of said conduit means;
   (c) a carrier gas supply means including an input line extending in fluid flow communication to said input of said conduit means to supply carrier gas thereto;
   (d) a mixture supply means including a mixture supply line means in fluid flow communication with said input line of said carrier gas supply means and with a reservoir containing the mixture of water and volatile product, said mixture supply means adapted to supply mixture to said input line for communication therethrough to said inlet of said conduit means, said mixture supply means comprising:
   1. a pump means to convey the mixture through said mixture supply line;

2. a mixture reservoir in fluid flow communication with said pump means to supply the mixture thereto;
3. an injection valve means to facilitate feeding of the mixture into said carrier gas input line, said injection valve means adapted to intermittently supply charges of mixture to said input line; and
4. a capillary restriction means positioned between said injection valve means and said carrier input line to minimize back flow therethrough and to minimize volatizing of the mixture except when a charge of mixture is being fed therethrough by said injection valve means;

(e) a product gathering means including an outlet line in fluid flow communication with said outlet of said conduit means, said product gathering means comprising:
1. a flow control valve means adjacent said outlet of said conduit means to control flow therethrough;
2. a cooling means to condense the volatilized product; and
3. a carrier gas vent to release the carrier gas after the product has been collected;

(f) a reverse flow means adapted to selectively reverse the flow of carrier gas through said continuous polymeric solid within said conduit means to withdraw the water accumulated therein, said reverse flow means being responsive to actuate after a pre-determined time delay subsequent to the supplying of a volatilized charge of mixture wherein the delay is long enough to allow the product within the mixture charge to be gathered by said product gathering means and short enough to have the water still retained within the adsorbing continuous polymeric solid, said reverse flow means comprising:
1. a reverse flow line extending from said carrier gas input line to said outlet of said conduit means;
2. a water line in fluid flow communication with said carrier gas input line adjacent said inlet of said conduit means, said water line adapted to gather water expelled through said inlet during reverse flow through said conduit means;
3. a first valve means positioned within said carrier gas input line upstream of said water line, said first valve means being normally opened and adapted to close responsive to actuation of said reverse flow means;
4. a second valve means positioned within said reverse flow line, said second valve means being normally closed and adapted to open responsive to actuation of said reverse flow means;
5. a third valve means positioned within said water line, said third valve means being normally closed and adapted to open responsive to actuation of said reverse flow means;

(g) a heating means positioned adjacent said conduit means to control the temperature thereof and positioned adjacent said carrier gas input line at the location of fluid flow connection to said mixture supply line to facilitate the volatilizing of the mixture into the carrier gas; and (h) a metal wool packing located within said carrier gas input adjacent connection to said mixture supply line to facilitate volatilizing of the mixture into the carrier gas.

18. A continuous reciprocating process for preparative chromatographic separation of unwanted volatile species from a volatile product comprising:
(a) introducing a charge of mixture of volatile species and volatile product into a carrier gas supply;
(b) volatilizing the charge of mixture, said volatilizing and said introducing comprises injecting the mixture into the carrier gas with an injection valve, said injecting being performed through a capillary tube into the carrier gas to prevent back flow and to minimize any additional volatilizing of material after the original charge has been introduced into the carrier gas;
(c) pumping the mixture from a mixture reservoir to be introduced into the carrier gas;
(d) passing the carrier gas through a conduit containing a continuous polymeric solid to allow the volatile species to be adsorbed to the solid and to allow the volatile product to pass therethrough much more quickly;
(e) heating the continuous polymeric solid to control the flow rates therethrough and heating the carrier gas and the mixture to facilitate said volatilizing;
(f) collecting the product after passage through the conduit, said collecting of the product further including cooling of the product after passing out of the conduit for condensing thereof;
(g) collecting the volatile species expelled from the conduit including venting of the collected water to the atmospheric environment to facilitate said collecting; and
(h) applying the carrier gas to the conduit in a reverse direction to expel the adsorbed volatile species therefrom back through the original direction in which the mixture passed into the conduit to make the conduit ready to receive a new charge of mixture.

19. A continuous flow apparatus for continuous preparative chromatographic separation of unwanted volatile species from volatile product comprising:
(a) a conduit having a generally circular configuration and defining an inlet and an outlet;
(b) a closed loop of continuous polymeric solid extending through said conduit, and being continuously moving therethrough;
(c) a drive means adapted to drive said closed loop through said conduit continuously at a speed less than the migration speed of the volatile product through the polymeric solid and greater than the migration speed of the volatile species through the polymeric solid, the direction of drive of said closed loop being from said outlet toward said inlet along the flow path of product therethrough;
(d) a mixture supply means to supply a vaporized mixture of volatile species and volatile product;
(e) a carrier gas supply means adapted to receive the mixture from said mixture supply means, said carrier gas supply means being in fluid flow communication with said inlet with the carrier gas being movable through said conduit means to said outlet in a direction upstream counter to the movement direction of said closed loop of continuous polymeric material, said volatile product responsive to be carried by the carrier gas upstream from said inlet directly to said outlet since the migration speed thereof through said loop is greater than the speed of movement of said loop from said outlet toward said inlet;

(f) a volatile species expelling means positioned downstream of said inlet and adapted to receive the volatile species absorbed within said moving closed loop; and (g) a product collecting means in fluid flow communication with said outlet to receive carrier gas and volatilized product therefrom.

20. The apparatus as defined in claim 19 further including a first constriction means located downstream of said inlet to minimize the tendency of carrier gas to flow downstream from said inlet.

21. The apparatus as defined in claim 19 further including a first bucking gas supply in fluid flow communication with said conduit downstream of said inlet to minimize the tendency of carrier gas to flow downstream from said inlet.

22. The apparatus as defined in claim 19 further comprising a second constriction means located upstream of said outlet to minimize the tendency of carrier gas to flow upstream of said outlet.

23. The apparatus as defined in claim 19 further comprising a second bucking gas supply located upstream of said outlet to minimize the tendency of carrier gas to flow upstream of said outlet.

24. The apparatus as defined in claim 19 further comprising a first heating means positioned adjacent said closed loop between said inlet and said outlet to control the flow rate of the volatile product therethrough.

25. The apparatus as defined in claim 23 wherein said conduit defines a first open end and a second open end wherein said volatile species expelling means includes a second heating means adjacent said moving closed loop of continuous polymeric solid adjacent said second bucking gas supply, said second heating means adapted to fully vaporize the volatile species within said loop and the portion of said bucking gas supply flowing counter to the direction of movement of said loop being adapted to blow the vaporized volatile species out of said second end of said conduit into the atmosphere to ready said loop to receive a new charge of mixture.

26. The apparatus as defined in claim 19 wherein said conduit defines a first open end through which said closed loop exits said conduit and a second open end into which said closed loop re-enters said conduit, said drive means being attached with respect to said closed loop for driving thereof outside of said conduit between said first end and said second end.

27. The apparatus as defined in claim 19 wherein said product collecting means includes a condenser means for condensing the vaporized product.

28. The apparatus as defined in claim 27 wherein said product collecting means includes a valve means for expelling the carrier gas from the condensed product.

29. The apparatus as defined in claim 19 wherein said carrier gas is air.

30. The apparatus as defined in claim 19 wherein said first bucking gas supply and said second bucking gas supply both supply air.

31. The apparatus as defined in claim 19 wherein said mixture supply means includes a mixture reservoir means.

32. The apparatus as defined in claim 19 wherein said mixture supply means includes a pump means.

33. The apparatus as defined in claim 19 wherein the volatile species is water.

34. The apparatus as defined in claim 19 wherein said mixture supply means comprises:

(a) an injection valve means for introducing the mixture of volatile species and volatile product; and (b) a capillary restriction means positioned between said injection valve means and said carrier gas supply to minimize back flow therethrough and to minimize volatilizing of the mixture except when a charge of mixture is being fed therethrough by said injection valve means.

35. The apparatus as defined in claim 19 wherein said conduit is circular in shape.

36. A continuous flow apparatus for preparative chromatographic separation of unwanted volatile species from volatile product comprising:

(a) a conduit having a generally circular configuration and defining a first open end and a second open end, said conduit also defining an inlet and an outlet;

(b) a closed loop of continuous polymeric solid extending through said conduit and through said first open end and said second open end, said closed loop being continuously moving therethrough;

(c) a first heating means positioned adjacent said closed loop between said inlet and said outlet to control the flow rate of volatile product therethrough;

(d) a drive means attached with respect to said closed loop for driving thereof outside of said conduit between said first open and said second open end, said drive means being adapted to drive said closed loop through said conduit continuously at a speed less than the migration speed of the product through the polymeric solid and greater than the migration speed of the volatile species through the polymeric solid, the direction of drive of said closed loop being from said outlet toward said inlet;

(e) a mixture supply means to supply a vaporized mixture of volatile species and volatile product, said mixture supply means comprising:
 1. a mixture reservoir means for the supplying of charges of mixture of the volatile species and volatile product;
 2. a pump means for withdrawing the mixture from said mixture reservoir;
 3. an injection valve means for controlling the introduction of the pumped mixture;

(f) a carrier gas supply means for supplying air adapted to receive the mixture from said mixture supply means, said carrier gas supply means being in fluid flow communication with said inlet with the carrier gas being movable through said conduit means to said outlet in a direction upstream counter to the movement direction of said closed loop of continuous polymeric material, said volatile product responsive to be carried by the carrier gas upstream from said inlet directly to said outlet since the migration speed thereof through said loop is greater than the speed of movement of said loop from said outlet toward said inlet;

(g) a first constriction means located downstream of said inlet to minimize the tendency of carrier gas to flow downstream of said inlet;

(h) a first bucking gas supply in fluid flow communication with said conduit downstream of said inlet to minimize the tendency of carrier gas to flow downstream from said inlet;

(i) a second constriction means located upstream of said outlet to minimize the tendency of carrier gas to flow upstream of said outlet;

(j) a second bucking gas supply located upstream of said outlet to minimize the tendency of carrier gas to flow upstream of said outlet;

(k) a volatile species expelling means positioned downstream of said inlet and adapted to receive the volatile species adsorbed within said moving closed loop, said volatile species expelling means including a second heating means positioned adjacent said moving closed loop of continuous polymeric solid between said second bucking gas supply and said second end of said conduit, said second heating means adapted to fully vaporize the volatile species within said loop and the portion of said bucking gas supply flowing counter to the direction of movement of said loop being adapted to blow the volatile species out of said second end of said conduit into the atmosphere to ready said loop to receive a new charge of mixture; and (l) a product collecting means in fluid flow communication with said outlet to receive carrier gas and volatilized product therefrom, said product collecting means including a condenser means for condensing vaporized product and a valve means for expelling the carrier gas from the condensed product.

37. A continuous process for chromatographically separating unwanted water from volatile product comprising:

(a) supplying a charge of mixture of water and volatile product into a stream of carrier gas, said supplying including pumping the mixture from a reservoir and vaporizing of the mixture by passing it through an injection valve means;

(b) passing the carrier gas stream into the inlet of a conduit containing a closed loop of continuous polymeric solid wherein the conduit has an inlet and an outlet;

(c) urging the carrier gas toward the outlet for expelling therethrough;

(d) continuously moving the closed loop through the conduit in a direction from the outlet toward the inlet at a velocity greater than the migration velocity of water through the polymeric solid and less than the velocity of migration of the volatile product through the polymeric solid to cause the water to be carried from the inlet downstream with the moving loop and the carrier gas and volatile product to move upstream counter to the direction of movement of the loop and out the outlet;

(e) constricting the conduit downstream of the inlet to encourage flow of carrier gas from the inlet toward the outlet;

(f) applying a bucking gas supply downstream of the inlet to encourage flow of carrier gas from the inlet toward the outlet;

(g) constricting the conduit upstream of the outlet to encourage the carrier gas to flow through the outlet;

(h) applying a bucking gas supply upstream of the outlet to encourage the carrier gas to flow through the outlet;

(i) expelling the water continuously at a location downstream of the inlet, said expelling including the heating of the closed loop adjacent an open end of the conduit to vaporize the water to facilitate expelling thereof;

(j) collecting the product at the outlet of the conduit, said collecting including condensing of the volatile product and exhausting of the carrier gas; and (k) heating the closed loop of polymeric solid to control the flow of carrier gas and mixture therethrough.

* * * * *

UNITED STATES PATENT AND TRADEMARK OFFICE
CERTIFICATE OF CORRECTION

PATENT NO. : 4,302,222
DATED : Nov. 24, 1981
INVENTOR(S) : Bernard Miller; Henry L. Friedman; Charles H. Meiser, Jr.

It is certified that error appears in the above-identified patent and that said Letters Patent are hereby corrected as shown below:

In Col. 1, Line 15 delete "absorbent" and insert therefor --adsorbent--

In Col. 1, Line 30 delete "absorbent" and insert therefor --adsorbent--

In Col. 6, Line 30 delete "114" and insert therefor --124--

In Col. 8, Line 14 delete "24" and insert therefor --224--

In Col. 15, Line 3; Claim 19f delete "absorbed" and insert therefor --adsorbed--

Signed and Sealed this

Twenty-seventh Day of April 1982

[SEAL]

Attest:

GERALD J. MOSSINGHOFF

Attesting Officer

Commissioner of Patents and Trademarks